(12) United States Patent
Murayama et al.

(10) Patent No.: US 9,873,619 B2
(45) Date of Patent: Jan. 23, 2018

(54) APPARATUS FOR MEASURING HYDROXYL RADICALS AND LIQUID TREATMENT APPARATUS

(71) Applicant: Kabushiki Kaisha Toshiba, Minato-ku (JP)

(72) Inventors: Seiichi Murayama, Fuchu (JP); Norimitsu Abe, Kawasaki (JP); Takeshi Ide, Kunitachi (JP); Ryoichi Arimura, Musashino (JP); Kie Kubo, Toshima (JP); Kenji Takeuchi, Fuchu (JP); Takahiro Soma, Kawasaki (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 160 days.

(21) Appl. No.: 14/758,046

(22) PCT Filed: Sep. 12, 2013

(86) PCT No.: PCT/JP2013/074765
§ 371 (c)(1),
(2) Date: Jun. 26, 2015

(87) PCT Pub. No.: WO2014/103440
PCT Pub. Date: Jul. 3, 2014

(65) Prior Publication Data
US 2015/0353382 A1    Dec. 10, 2015

(30) Foreign Application Priority Data

Dec. 28, 2012  (JP) ................................. 2012-288956

(51) Int. Cl.
*G01N 21/00*  (2006.01)
*C02F 1/32*  (2006.01)
(Continued)

(52) U.S. Cl.
CPC ............. *C02F 1/32* (2013.01); *G01N 21/631* (2013.01); *G01N 21/75* (2013.01); *C02F 1/78* (2013.01);
(Continued)

(58) Field of Classification Search
None
See application file for complete search history.

(56) References Cited

U.S. PATENT DOCUMENTS

| 4,012,321 A * | 3/1977 | Koubek | .................. C02F 1/722 |
| | | | 210/748.15 |
| 2004/0126279 A1 * | 7/2004 | Renzi | ................ B01L 3/502715 |
| | | | 422/502 |

(Continued)

FOREIGN PATENT DOCUMENTS

| JP | H04-320696 A | 11/1992 |
| JP | H10-332667 A | 12/1998 |

(Continued)

OTHER PUBLICATIONS

Machine Translation of JP 2001-259666 to Kamimura etl al (original submitted by applicant).*

(Continued)

*Primary Examiner* — Jill Warden
*Assistant Examiner* — Brittany Fisher
(74) *Attorney, Agent, or Firm* — Oblon, McClelland, Maier & Neustadt, L.L.P.

(57) ABSTRACT

According to one embodiment, an apparatus for measuring hydroxyl radicals that measures hydroxyl radicals produced by irradiating a liquid to be treated flowing through a channel in which an ultraviolet lamp is arranged with ultraviolet rays, the apparatus includes a diverting unit, a reagent adding unit, and a measuring unit. The diverting unit has a diverting channel that diverts the liquid to be treated (Continued)

before being irradiated with the ultraviolet rays from the channel and part of which is arranged at a position enabling the liquid to be treated within the channel to be irradiated with the ultraviolet rays. The reagent adding unit adds a hydroxyl radical measuring reagent to the diverted liquid to be treated. The measuring unit irradiates the diverted liquid to be treated with the ultraviolet rays and measures the amount of hydroxyl radicals produced based on a change in the hydroxyl radical measuring reagent between before and after the irradiation with the ultraviolet rays.

6 Claims, 12 Drawing Sheets

(51) Int. Cl.
| | | |
|---|---|---|
| *G01N 21/63* | (2006.01) | |
| *G01N 21/75* | (2006.01) | |
| *G01N 21/64* | (2006.01) | |
| *C02F 1/78* | (2006.01) | |

(52) U.S. Cl.
CPC .... *C02F 2201/322* (2013.01); *C02F 2209/00* (2013.01); *C02F 2303/04* (2013.01); *C02F 2305/023* (2013.01); *G01N 2021/632* (2013.01); *G01N 2021/6417* (2013.01)

(56) References Cited

U.S. PATENT DOCUMENTS

| | | | |
|---|---|---|---|
| 2011/0180485 A1* | 7/2011 | Sitkiewitz | C02F 9/00 210/739 |
| 2012/0231549 A1* | 9/2012 | Miller | G01N 21/33 436/131 |

FOREIGN PATENT DOCUMENTS

| | | |
|---|---|---|
| JP | 2000-180430 A | 6/2000 |
| JP | 2000-279977 A | 10/2000 |
| JP | 2001-259666 A | 9/2001 |
| JP | 2012-98114 A | 5/2012 |

OTHER PUBLICATIONS

Machine Transation of JP 2000-180430 to Kato et al (original submitted by application).*
Machine Transation of JP 2012-098114 to Kanazawa et al (original submitted by applicant).*
International Search Report dated Oct. 22, 2013, in PCT/JP2013/074765, filed Sep. 12, 2013.

* cited by examiner

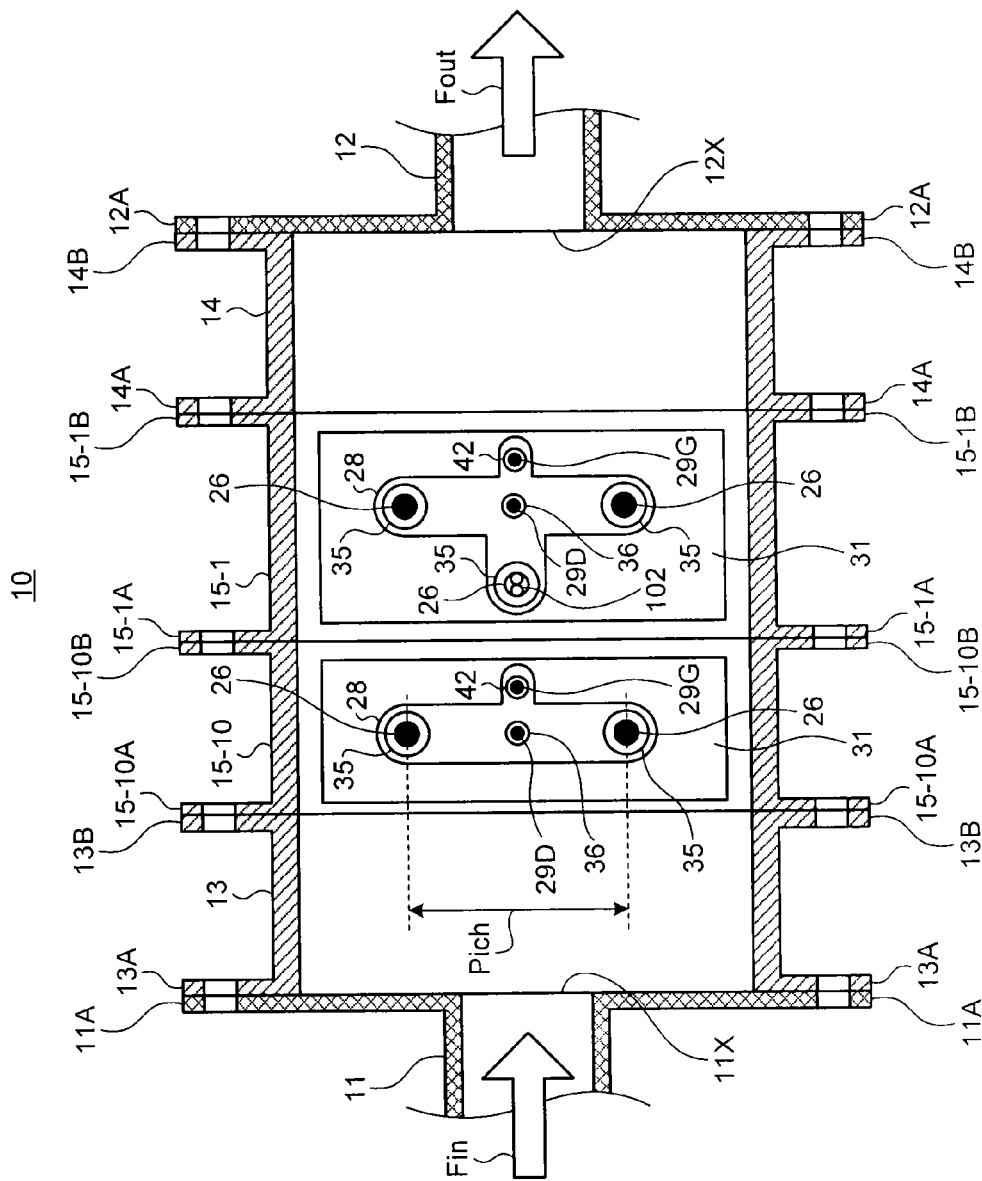

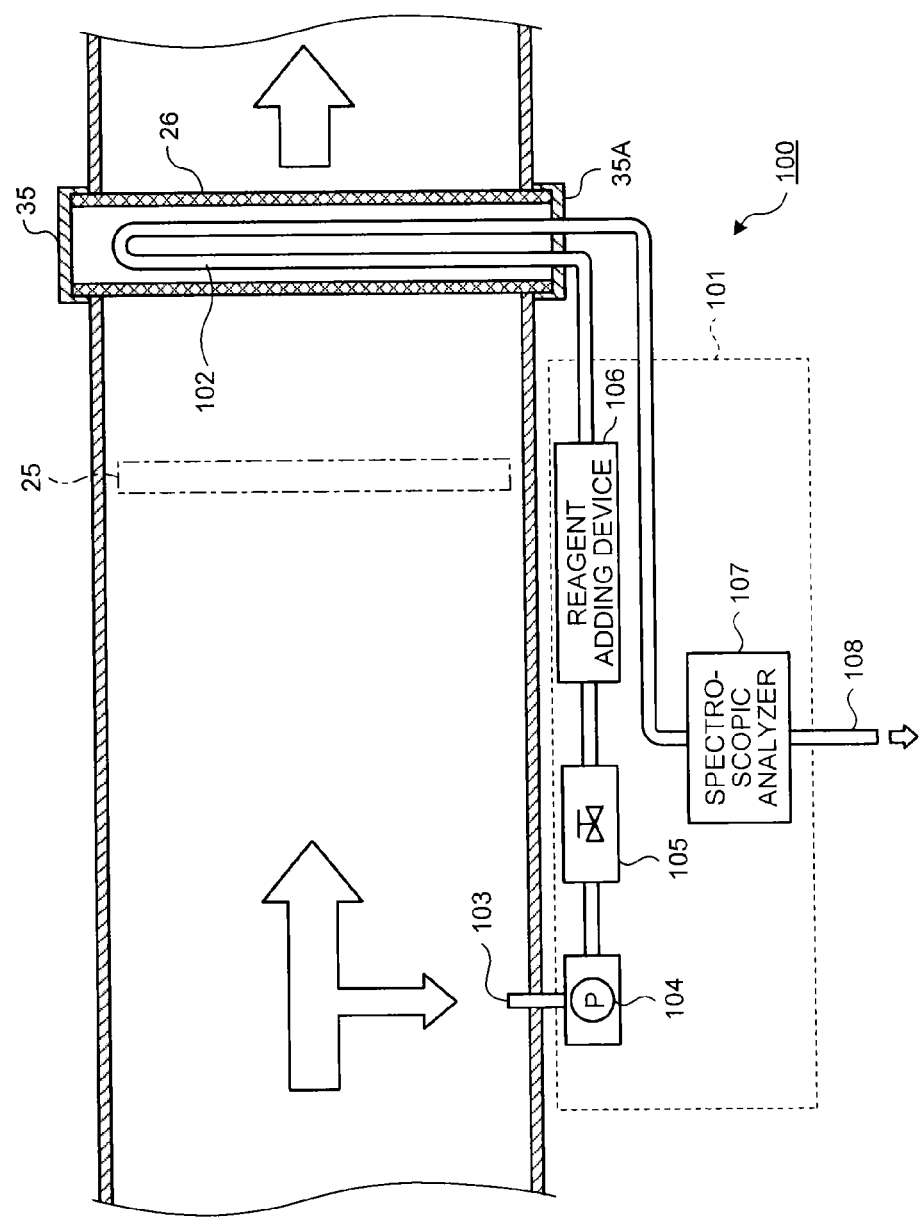

US 9,873,619 B2

APPARATUS FOR MEASURING HYDROXYL RADICALS AND LIQUID TREATMENT APPARATUS

CROSS-REFERENCE TO RELATED APPLICATIONS

This application is national stage application of International Application No. PCT/JP2013/074765, filed Sep. 12, 2013, which designates the United States, incorporated herein by reference, and which claims the benefit of priority from Japanese Patent Application No. 2012-288956, filed Dec. 28, 2012, the entire contents of which are incorporated herein by reference.

FIELD

Embodiments described herein relate generally to an apparatus for measuring hydroxyl radicals and a liquid treatment apparatus.

BACKGROUND

Conventionally, ozone has been used to perform sterilization and disinfection of treated water of water supply and sewerage (tap water, ground water, or the like), deodorization and decolorization of industrial water, bleaching of pulp, sterilization of medical equipment, or the like.

However, although even oxidization by ozone has been able to perform hydrophilization and degradation, it has not been able to perform mineralization. Hardly decomposable organic matter such as dioxin and 1,4-dioxane has not been able to be decomposed by oxidation by ozone.

Given these circumstances, in decomposing these substances, it is general to perform oxidative decomposition using the hydroxyl radical, which has stronger oxidizing power than ozone.

For the formation of hydroxyl radicals, generally used methods in water treatment include a method that irradiates ozone-containing water with ultraviolet rays, a method that adds ozone to hydrogen peroxide-containing water, a method that irradiates hydrogen peroxide-containing water with ultraviolet rays, and a method that uses all hydrogen peroxide, ozone, and ultraviolet rays in combination.

Two or more of hydrogen peroxide, ozone, and ultraviolet rays are thus used in combination, a water treatment apparatus using the strong oxidizing power of the hydroxyl radical has a problem in that an initial cost and an operating cost are high.

In view of the above circumstances, a design of an apparatus that efficiently produces hydroxyl radicals and that causes the produced hydroxyl radicals to efficiently contribute to reaction can reduce the initial cost. It is desired to provide operation control with which sufficient hydroxyl radicals are produced for treatment.

Given this situation, if the concentration of hydroxyl radicals is continuously measured, efficient operation control is achieved. However, although hydroxyl radicals have strong oxidizing power, they have short lifetime and are required to be measured on the spot after being produced; the measurement is thus difficult under the present circumstances.

A method that produces a spin adduct using a spin trapping agent such as DMPO for measuring hydroxyl radicals and performs measurement by ESR has been proposed as a technique for measuring hydroxyl radicals.

A method that, using a characteristic of indoxyl-β-D-glucuronide as a component present in urine or blood easily reacting with hydroxyl radicals, measures the concentration of indoxyl-β-D-glucuronide in terms of fluorescence intensity or absorbance has been proposed as a medical application; and both methods use reagents.

However, both of the above methods have difficulty in continuously measuring hydroxyl radicals produced in an apparatus.

The present invention has been made in view of the above circumstances, and an object of embodiments is to provide an apparatus for measuring hydroxyl radicals and a liquid treatment apparatus that can continuously measure hydroxyl radicals without influencing the water quality or the like of a treatment system in water treatment facilities or the like.

An apparatus for measuring hydroxyl radicals of an embodiment is an apparatus for measuring hydroxyl radicals that measures hydroxyl radicals produced by irradiating a liquid to be treated flowing through a channel in which an ultraviolet lamp is installed with ultraviolet rays.

A diverting unit has a diverting channel that diverts the liquid to be treated before being irradiated with ultraviolet rays from the channel and part of which is arranged at a position enabling the liquid to be treated within the channel to be irradiated with the ultraviolet rays.

A reagent adding unit adds a hydroxyl radical measuring reagent to the diverted liquid to be treated.

A measuring unit irradiates the diverted liquid to be treated with the ultraviolet rays and measures the amount of hydroxyl radicals produced based on a change in the hydroxyl radical measuring reagent between before and after the irradiation with the ultraviolet rays.

BRIEF DESCRIPTION OF DRAWINGS

FIG. 2 is a sectional schematic diagram (an elevational view) of the ultraviolet water treatment apparatus in which the apparatus for measuring hydroxyl radicals is installed in the first embodiment;

FIG. 3 is an illustrative diagram of a diagrammatic configuration of the apparatus for measuring hydroxyl radicals in the first embodiment;

DETAILED DESCRIPTION

In general, according to one embodiment, an apparatus for measuring hydroxyl radicals that measures hydroxyl radicals produced by irradiating a liquid to be treated flowing through a channel in which an ultraviolet lamp is arranged with ultraviolet rays, the apparatus comprises a diverting unit, a reagent adding unit, and a measuring unit. The diverting unit has a diverting channel that diverts the liquid to be treated before being irradiated with the ultraviolet rays from the channel and part of which is arranged at a position enabling the liquid to be treated within the channel to be irradiated with the ultraviolet rays. The reagent adding unit adds a hydroxyl radical measuring reagent to the diverted liquid to be treated. The measuring unit irradiates the diverted liquid to be treated with the ultraviolet rays and measures the amount of hydroxyl radicals produced based on a change in the hydroxyl radical measuring reagent between before and after the irradiation with the ultraviolet rays.

[1] First Embodiment

Figure 1:
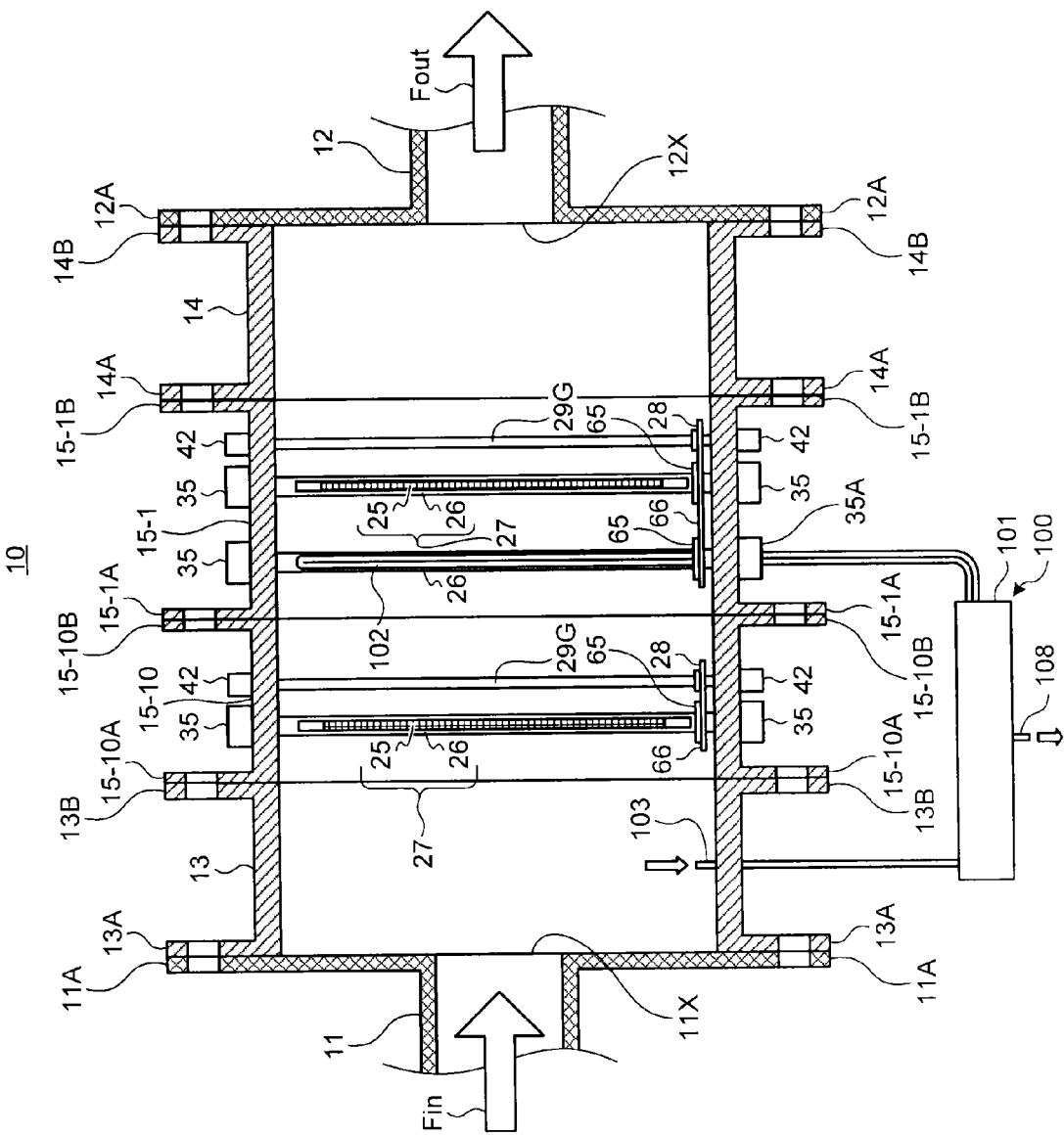
FIG. 1 is a sectional schematic diagram (a plan view) of an ultraviolet water treatment apparatus in which an apparatus for measuring hydroxyl radicals is installed according to a first embodiment.

FIG. 1 is a sectional schematic view (a plan view) of an ultraviolet water treatment apparatus in which an apparatus for measuring hydroxyl radicals of a first embodiment is installed.

FIG. 2 is a sectional schematic view (an elevational view) of the ultraviolet water treatment apparatus in which the apparatus for measuring hydroxyl radicals of the first embodiment is installed.

An inflow side connection pipe 11 through which water to be treated as a liquid to be treaded flows in is connected to the upstream side of an ultraviolet water treatment apparatus 10 as a liquid treatment apparatus, whereas an outflow side connection pipe 12 through which the treated water flows out is connected to the downstream side thereof.

The ultraviolet water treatment apparatus 10 broadly includes an inlet pipe 13 connected to the inflow side connection pipe 11 having an inflow port 11X, an outlet pipe 14 connected to the outflow side connection pipe 12 having an outflow port 12X, ultraviolet irradiation units 15-1 and 15-10 connected to between the inlet pipe 13 and the outlet pipe 14, and an apparatus 100 for measuring hydroxyl radicals.

The apparatus 100 for measuring hydroxyl radicals includes an apparatus main body 101 for measuring hydroxyl radicals and a diverting pipe 102 for measurement that is connected to the apparatus main body 101 for measuring hydroxyl radicals and is integrally incorporated into the ultraviolet irradiation unit 15-1.

The inflow side connection pipe 11, the inlet pipe 13, the outlet pipe 14, the ultraviolet irradiation unit 15-10, the ultraviolet irradiation unit 15-1, and the outflow side connection pipe 12 are coaxially arranged to form a water flowing barrel.

The inlet pipe 13 is mounted on a flange 11A of the inflow side connection pipe 11 through a flange 13A. In addition, the inlet pipe 13 is mounted on a flange 15-10A of the ultraviolet irradiation unit 15-10 through a flange 13B.

A flange 15-10B of the ultraviolet irradiation unit 15-10 is provided with a flange 15-1A of the ultraviolet irradiation unit 15-1.

A flange 15-1B of the ultraviolet irradiation unit 15-1 is provided with a flange 14A of the outlet pipe 14.

A flange 14B of the outlet pipe 14 is provided with a flange 12A of the outflow side connection pipe 12.

The following describes a configuration of the ultraviolet irradiation units.

The ultraviolet irradiation units 15-1 and 15-10 have box-shaped casings that are larger than the diameters of the inlet pipe 13 and the outlet pipe 14 and are connected to each other by welding. A part around the connecting part is ribbed in order to reinforce the ultraviolet irradiation units 15-1 and 15-10.

As illustrated in FIG. 1, the inlet pipe 13 is connected to the upstream side of the ultraviolet irradiation unit 15-10. The outlet pipe 14 is connected to the downstream side of the ultraviolet irradiation unit 15-1.

The front of the ultraviolet irradiation unit 15-1 is provided with an opening so that an ultraviolet irradiation module 15-X described below can be installed. The front of the ultraviolet irradiation unit 15-10 is provided with an opening so that an ultraviolet irradiation module 15-X1 described below can be installed. A lid having a watertight structure with watertight rubber packing (not illustrated) is screw-fixed to the ultraviolet irradiation module 15-X or the ultraviolet irradiation module 15-X1. That is, by removing the screw-fixed lid, the ultraviolet irradiation module 15-X or the ultraviolet irradiation module 15-X1 is removed so as to open the interior of the ultraviolet irradiation unit 15-1 or the ultraviolet irradiation unit 15-10 as needed.

Protective pipes 26 are fixed by fixing members 35 on the back side of lids 31 and the ultraviolet irradiation units 15-1 and 15-10. Similarly, screw-shaped cleaning device drive shafts 29D for driving cleaning devices 28 are fixed by fixing members 36 on the back side of the lids 31 and the ultraviolet irradiation units 15-1 and 15-10. Guide rails 29G are fixed by guide rail fixing members 42 on the back side of the lids 31 and the ultraviolet irradiation units 15-1 and 15-10.

In this case, the protective pipes 26, the cleaning device drive shafts 29D, and the guide rails 29G are arranged in parallel to each other. In addition, the protective pipes 26, the cleaning device drive shafts 29D, and the guide rails 29G are arranged so as to extend in a direction perpendicular to a central axis of the inflow side connection pipe 11 and the outflow side connection pipe 12. The ultraviolet irradiation unit 15-10 and the ultraviolet irradiation unit 15-1 can have a shape that causes the water to be treated to flow only near ultraviolet lamps so as to gain larger amounts of ultraviolet rays received to achieve accelerated oxidation.

The following describes a configuration of the apparatus 100 for measuring hydroxyl radicals.

FIG. 3 is an illustrative diagram of a diagrammatic configuration of the apparatus for measuring hydroxyl radicals of the first embodiment.

The apparatus main body 101 for measuring hydroxyl radicals forming the apparatus 100 for measuring hydroxyl radicals includes a pump 104 for diverting and taking in the water to be treated as the liquid to be treated flowing through the water flowing barrel before being irradiated with ultraviolet rays through an intake pipe 103 and a shutoff valve 105 for shutting off the intake of the water to be treated by the pump 104 in accordance with needs such as maintenance.

The apparatus 100 for measuring hydroxyl radicals includes a reagent adding device 106 for adding a hydroxyl radical measuring reagent to the water to be treated taken in, a spectroscopic analyzer 107 to which the water to be treated with the hydroxyl radical measuring reagent added thereto flows in after flowing through the diverting pipe 102 for measurement and being irradiated with ultraviolet rays and that spectroscopically analyses the amount (concentration) of hydroxyl radicals produced, and a discharge pipe 108 that discharges the water to be treated with the reagent added thereto after the spectroscopic analysis.

In the above description, the reason why the water to be treated is diverted and taken in through the intake pipe 103 before being irradiated with ultraviolet rays is to avoid the water to be treated from receiving ultraviolet irradiation before the addition of the measuring reagent and avoid hydroxyl radicals from being produced.

In the above configuration, the diverting pipe 102 for measurement is formed of an ultraviolet transmitting material such as quartz glass.

The following describes a mechanism by which hydroxyl radicals are produced within the water flowing barrel (reaction tank).

At least one pro-oxidant among hydrogen peroxide, ozone, and chlorine agents such as sodium hypochlorite is added in advance at the downstream side of the water flowing barrel (reaction tank). An addition mechanism therefor simply needs to have a general configuration, and a description thereof is omitted. The pro-oxidant added in advance by this addition mechanism is, after an appropriate contact time, flown in to the water flowing barrel (reaction tank) of the ultraviolet water treatment apparatus 10 in which ultraviolet lamps are installed.

Consequently, receiving ultraviolet irradiation from the ultraviolet lamps within the water flowing barrel (reaction tank) of the ultraviolet water treatment apparatus 10, hydroxyl radicals are produced, which oxidatively decompose substances such as organic substances contained in the water to be treated.

The formation of hydroxyl radicals by the reaction of ozone with ultraviolet rays follows the following reaction formulae.

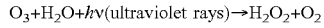

$O_3 + H_2O + h\nu(\text{ultraviolet rays}) \rightarrow H_2O_2 + O_2$

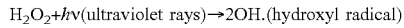

$H_2O_2 + h\nu(\text{ultraviolet rays}) \rightarrow 2OH\cdot(\text{hydroxyl radical})$ The formation of hydroxyl radicals by the reaction of hydrogen peroxide with ultraviolet rays follows the following reaction formula.

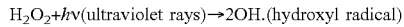

$H_2O_2 + h\nu(\text{ultraviolet rays}) \rightarrow 2OH\cdot(\text{hydroxyl radical})$ The following describes the hydroxyl radical measuring reagent added by the reagent adding device 106.

The hydroxyl radical measuring reagent is preferably a reagent that does not react with each of ultraviolet rays, ozone, hydrogen peroxide, and chlorine agents such as sodium hypochlorite individually, and that selectively reacts with hydroxyl radicals alone.

Examples thereof include a terephthalic acid solution, a dimethylsulfoxide solution (hereinafter, referred to as DMSO), and 5,5-dimethyl-1-pyrroline-N-oxide (DMPO).

The terephthalic acid solution changes into hydroxyterephthalic acid by hydroxyl radicals, which can be measured by fluorescence analysis as the spectroscopic analysis (excitation at 310 nm and fluorescence at 425 nm).

DMSO changes into methanesulfonic acid by hydroxyl radicals. Methanesulfonic acid is required to be measured by ion chromatography or the like. DMPO reacts with hydroxyl radicals to produce a spin adduct called DMPO-OH, and DMPO-OH is required to be measured by ESR.

In the present embodiment, hydroxyl radical concentration is required to be measured continuously and automatically, and a method that enables spectral measurement such as fluorescence analysis is preferable, with terephthalic acid used as the hydroxyl radical measuring reagent. The measurement is not limited to this method as far as treatment speed is sufficiently high and continuous treatment (including continuous batch treatment) is capable.

The following describes a configuration of the ultraviolet irradiation units.

FIG. 4 includes illustrative diagrams of an ultraviolet irradiation unit integrated with part of an apparatus for measuring hydroxyl radicals.

Figure 4A:
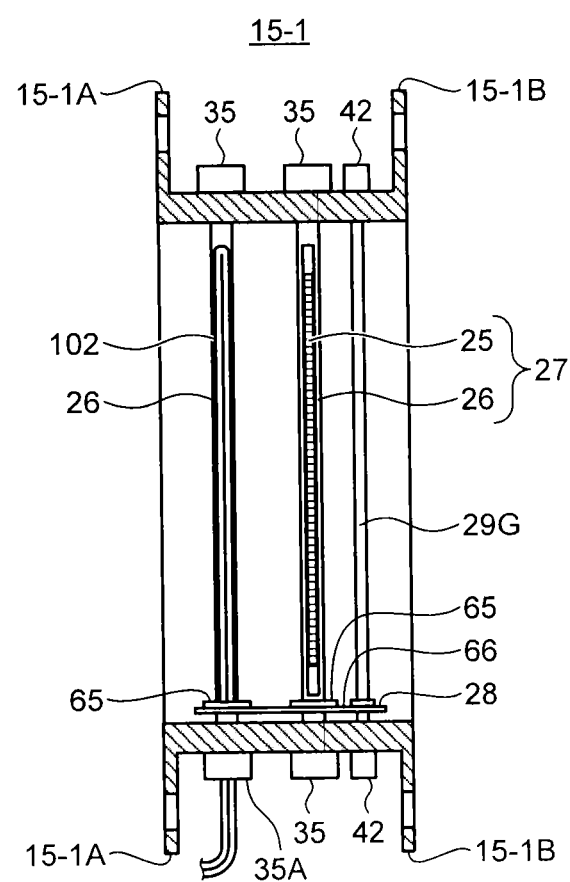
FIG. 4A is a sectional schematic diagram (a plan view) of an ultraviolet irradiation unit in the first embodiment.

FIG. 4A is a sectional schematic diagram (a plan view) of an ultraviolet irradiation unit.

Figure 4B:
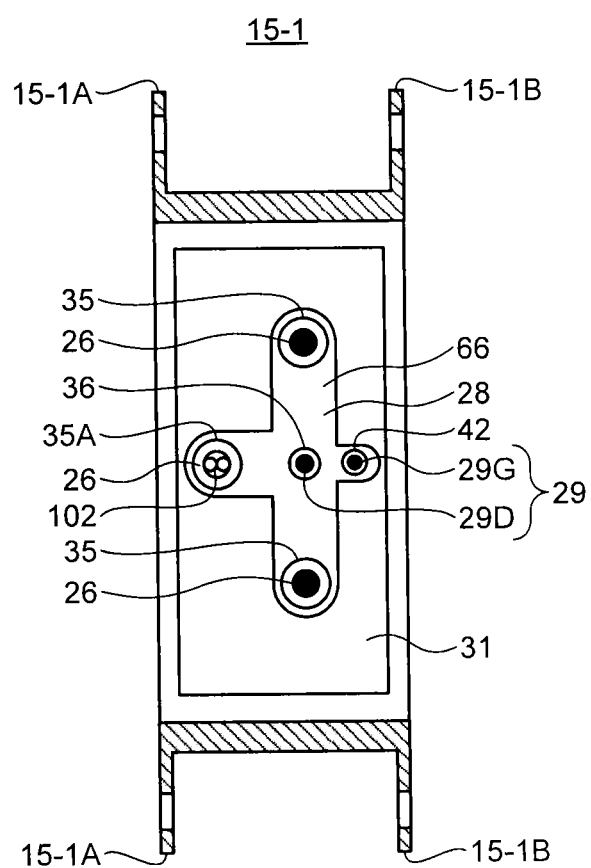
FIG. 4B is a sectional schematic diagram (an elevational view) of the ultraviolet irradiation unit in the first embodiment.

FIG. 4B is a sectional schematic diagram (an elevational view) of the ultraviolet irradiation unit.

The ultraviolet irradiation unit 15-1 includes two ultraviolet lamps 25, one protective pipe 26 housing the diverting pipe 102 for measurement, two ultraviolet irradiation pipes 27 having protective pipes 26 that protect the respective ultraviolet lamps 25, the cleaning device 28 that cleans all the protective pipes 26, and a cleaning device drive unit 29 that drives the cleaning device 28.

In the above configuration, the cleaning device 28 includes cleaning brushes 65 installed so as to rub the surfaces of the protective pipes 26 and a lamp protective pipe cleaning plate 66 that fixes the cleaning brushes 65. The cleaning brushes 65 and the lamp protective pipe cleaning plate 66 are fixed within the box-shaped ultraviolet irradiation unit 15-1 through the cleaning device drive shaft 29D and the guide rail 29G.

The cleaning device drive shafts 29D are rotatably supported on the back side of the front side lid 31 of the ultraviolet irradiation unit 15-1 and the ultraviolet irradiation units 15-1 and 15-10 by the fixing members 35 while maintaining watertightness of the ultraviolet irradiation units 15-1 and 15-10. In addition, a drive motor (not illustrated) is connected to one end of the cleaning device drive shafts 29D. Similarly, the guide rail 29G is fixed to the ultraviolet irradiation unit 15-1 by the guide rail fixing member 42.

Furthermore, the drive motor (not illustrated) rotates the cleaning device drive shaft 29D at certain time intervals, and the lamp protective pipe cleaning plate 66 moves in the axial direction (in the back and forth direction of FIG. 4B) of the protective pipes 26.

Figure 5:
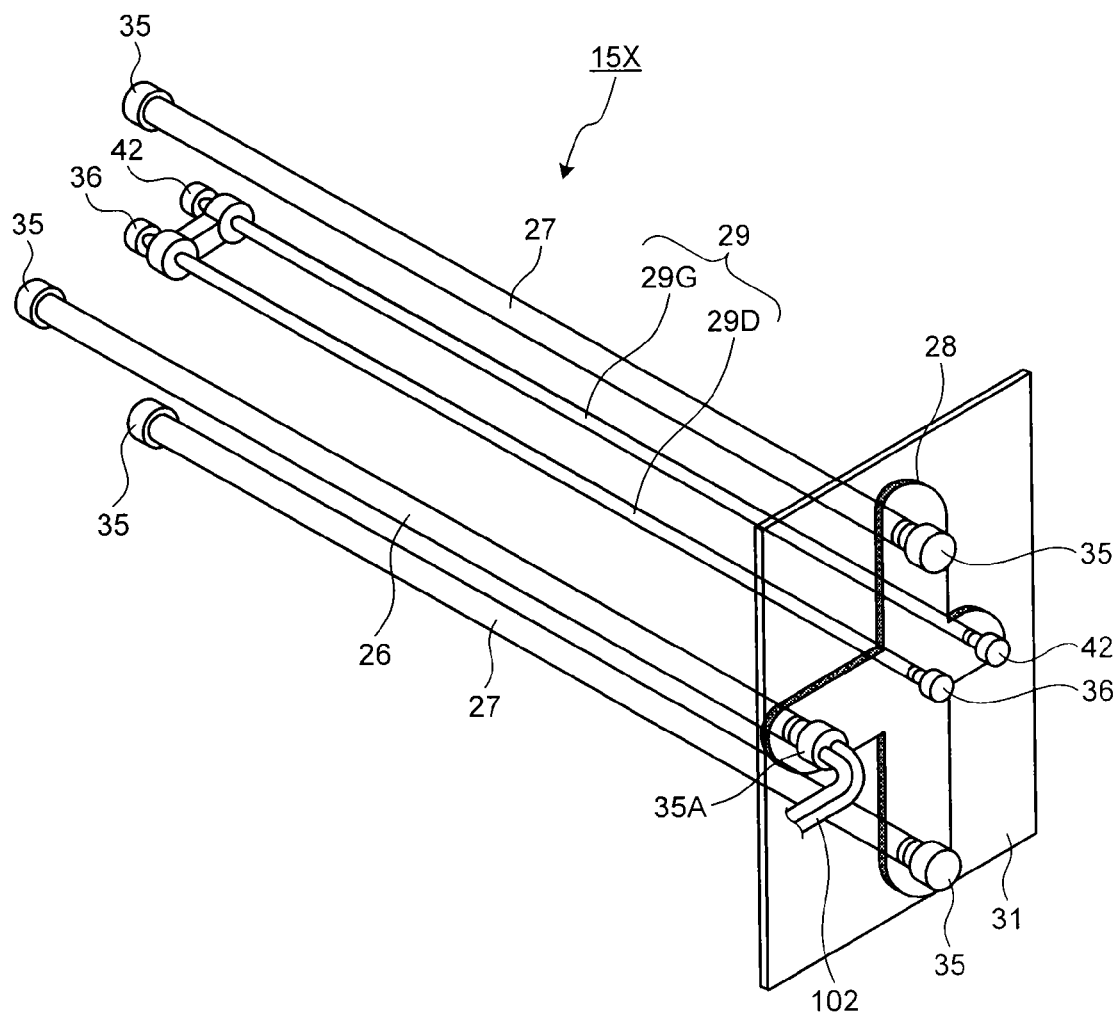
FIG. 5 is a perspective view of a diagrammatic configuration of an ultraviolet irradiation module in the first embodiment.

FIG. 5 is a perspective view of a diagrammatic configuration of an ultraviolet irradiation module.

As illustrated in FIG. 5, the ultraviolet lamps 25, the protective pipe 26 housing the diverting pipe 102 for measurement, the ultraviolet irradiation pipes 27, the cleaning device 28, and the cleaning device drive unit 29 are formed as an integrated ultraviolet irradiation module 15-X.

The following describes a configuration of another ultraviolet irradiation unit.

Figure 6A:
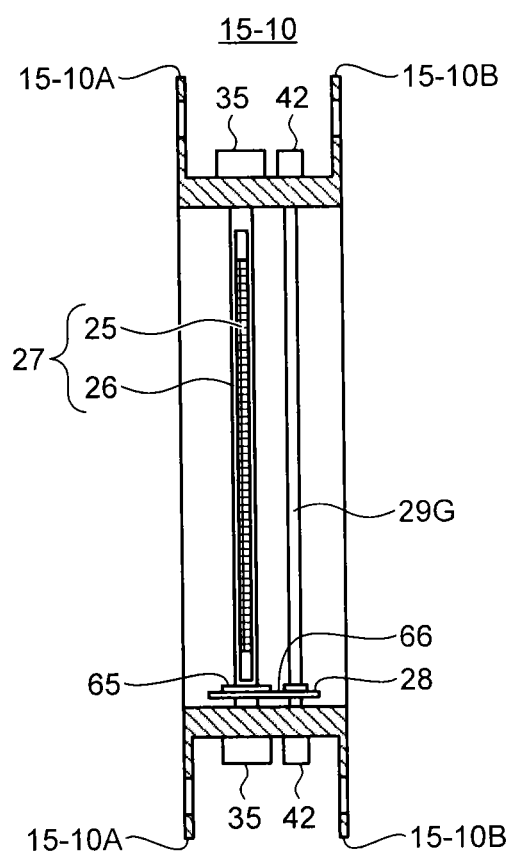
FIG. 6A is a sectional schematic diagram (a plan view) of an ultraviolet irradiation unit as another ultraviolet irradiation unit in the first embodiment.

FIG. 6A is a sectional schematic diagram (a plan view) of an ultraviolet irradiation unit as the another ultraviolet irradiation unit.

Figure 6B:
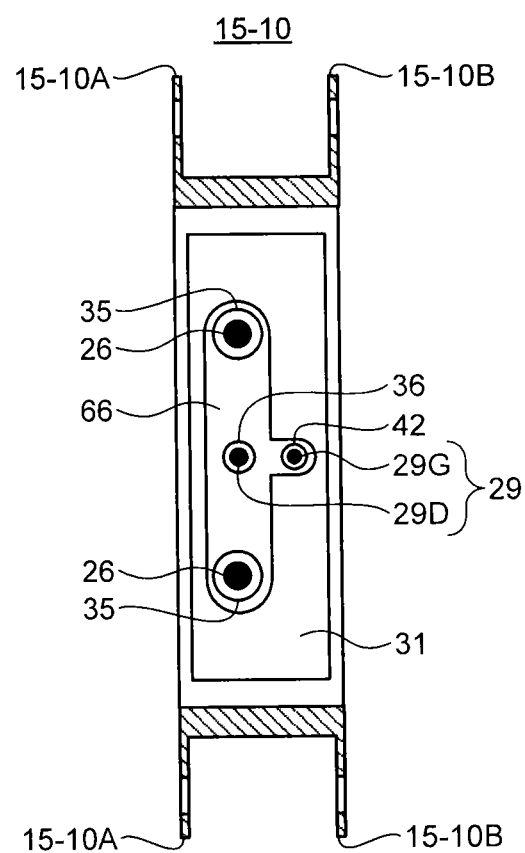
FIG. 6B is a sectional schematic diagram (an elevational view) of the ultraviolet irradiation unit as the another ultraviolet irradiation unit in the first embodiment.

FIG. 6B is a sectional schematic diagram (an elevational view) of the ultraviolet irradiation unit as the another ultraviolet irradiation unit.

In FIG. 6A and FIG. 6B, parts similar to those of FIG. 5 are attached with the same symbols.

The ultraviolet irradiation unit 15-10 includes the two ultraviolet lamps 25, the ultraviolet irradiation pipes 27 having the protective pipes 26 that protect the respective ultraviolet lamps 25, the cleaning device 28 that cleans all the protective pipes 26, and the cleaning device drive unit 29 that drives the cleaning device 28.

Figure 7:
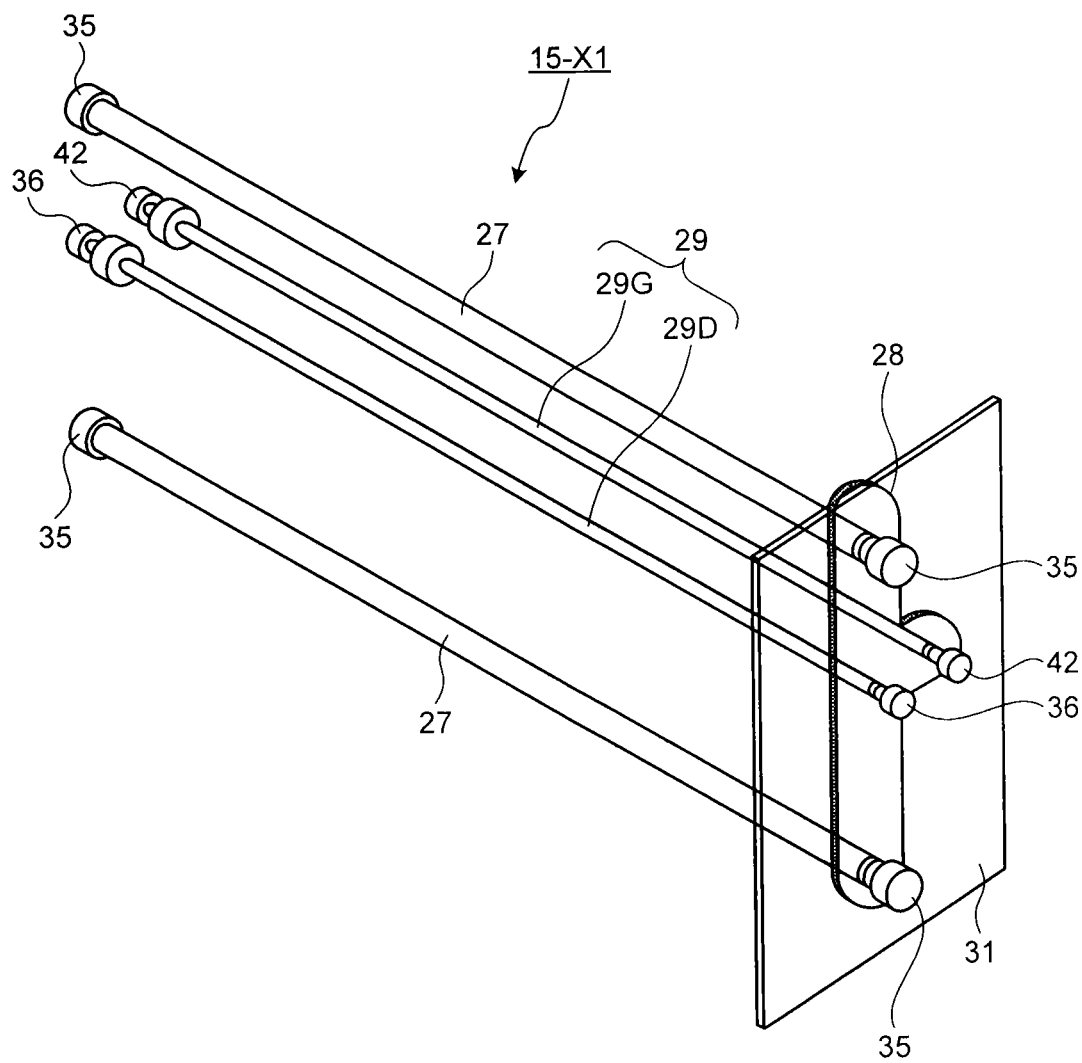
FIG. 7 is a perspective view of a diagrammatic configuration of another ultraviolet irradiation module in the first embodiment.

FIG. 7 is a perspective view of a diagrammatic configuration of another ultraviolet irradiation module.

As illustrated in FIG. 7, the ultraviolet lamps 25, the ultraviolet irradiation pipes 27, the cleaning device 28, and the cleaning device drive unit 29 are formed as an integrated ultraviolet irradiation module 15-X1.

The following describes operation in the embodiment.

At the upstream side, at least one pro-oxidant among hydrogen peroxide, ozone, and chlorine agents such as sodium hypochlorite is added to the water to be treated in advance.

The water to be treated that has flowed in from the inflow side connection pipe 11 successively flows in to the ultraviolet irradiation units 15-10 and 15-1 and comes into uniform contact with the ultraviolet lamps 25 (the protective pipes 26).

Consequently, receiving ultraviolet irradiation from the ultraviolet lamps 25 within the water flowing barrel (reaction tank) of the ultraviolet water treatment apparatus 10, hydroxyl radicals are produced, which oxidatively decompose substances such as organic substances contained in the water to be treated and perform disinfection (sterilization) or oxidizing treatment on the water to be treated efficiently.

The treated water flows out through the outflow side connection pipe 12.

In parallel therewith, the pump 104 of the apparatus 100 for measuring hydroxyl radicals diverts and takes in the water to be treated flowing through the water flowing barrel through the intake pipe 103.

The water to be treated taken in flows in to the reagent adding device 106 through the shutoff valve 105.

The reagent adding device 106 then adds the hydroxyl radical measuring reagent to the water to be treated so as to give a certain concentration.

The water to be treated with the hydroxyl radical measuring reagent added thereto flows through the diverting pipe 102 for measurement, is irradiated with ultraviolet rays to produce hydroxyl radicals according to the above reaction formulae, and is guided to the spectroscopic analyzer 107.

In this situation, the amount of flow of the water to be treated flowing through the diverting pipe 102 for measurement per unit time and the concentration of the hydroxyl radical measuring reagent are set by the spectroscopic analyzer 107 in advance. The spectroscopic analyzer 107 then continuously spectroscopically analyzes the amount (concentration) of hydroxyl radicals produced. The analysis result is sent to a managing apparatus (not illustrated), is fed back, and is used for the control of the amount of ultraviolet irradiation, the control of the amount of flow of the water to be treated, or the like. In other words, the managing apparatus performs control so that the disinfection (sterilization) or oxidizing treatment on the water to be treated is performed as predetermined.

Thereafter, the water to be treated with the hydroxyl radical measuring reagent added thereto for which the spectroscopic analysis has been completed is not returned to the water flowing barrel and is discharged through the discharge pipe 108 or is subjected to waste liquid treatment as needed and is discharged.

As described above, the first embodiment can measure hydroxyl radials continuously without influencing the water quality or the like of a treatment system in water treatment facilities or the like.

The diverting pipe 102 for measurement has a structure housed in the protective pipe 26, and even during replacement or maintenance, the operation of the ultraviolet water treatment apparatus is continued, which improves the operation efficiency of the ultraviolet water treatment apparatus.

[2] Second Embodiment

Although the first embodiment employs a configuration in which the diverting pipe 102 for measurement is provided within the protective pipe 26, the present second embodiment employs a configuration in which the water to be treated for hydroxyl radical measurement flows directly through the protective pipe 26.

Figure 8:
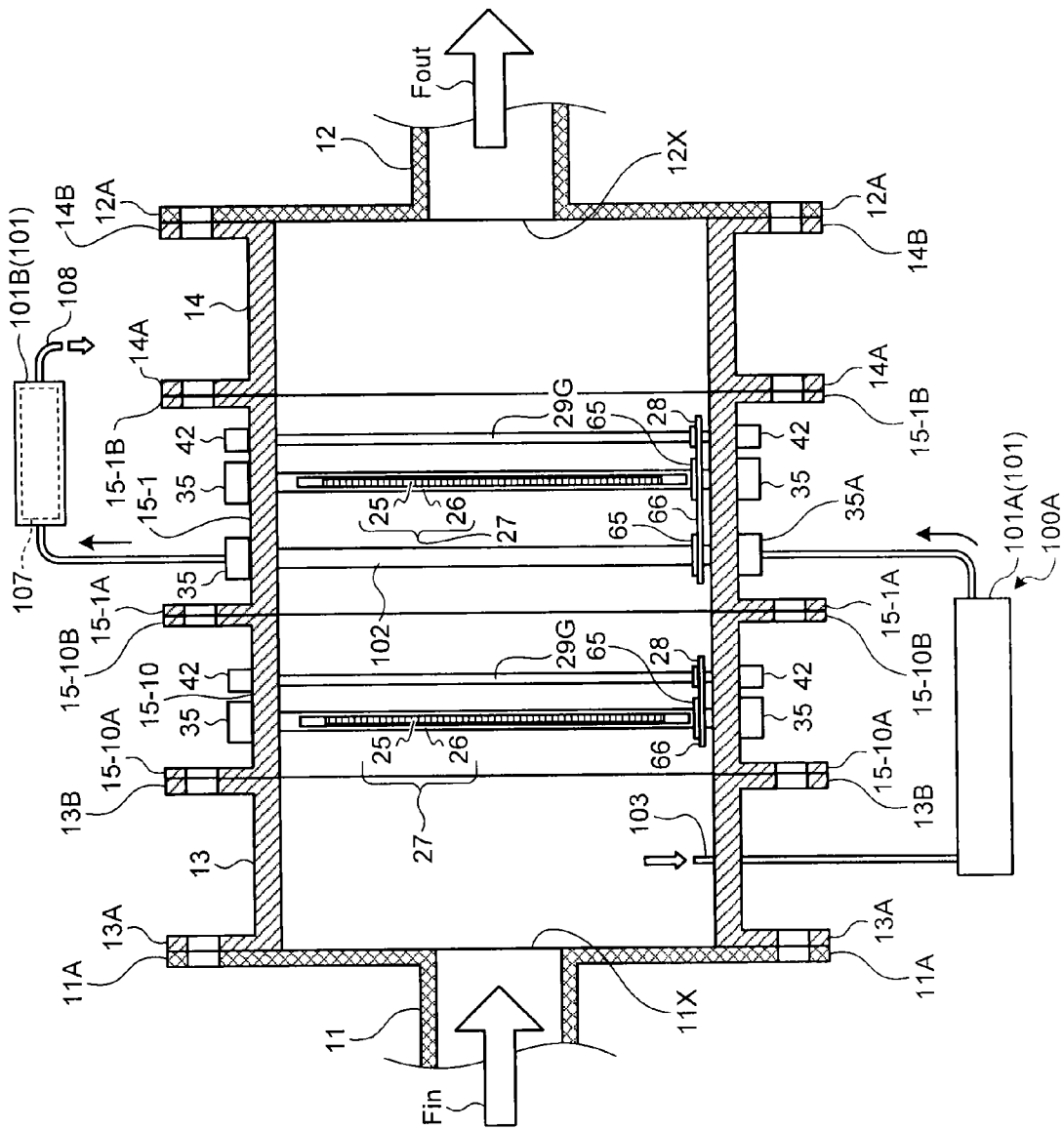
FIG. 8 is a sectional schematic diagram (a plan view) of an ultraviolet water treatment apparatus in which an apparatus for measuring hydroxyl radicals is installed according to a second embodiment.

FIG. 8 is a sectional schematic diagram (a plan view) of an ultraviolet water treatment apparatus in which an apparatus for measuring hydroxyl radicals of the second embodiment is installed.

Figure 9:
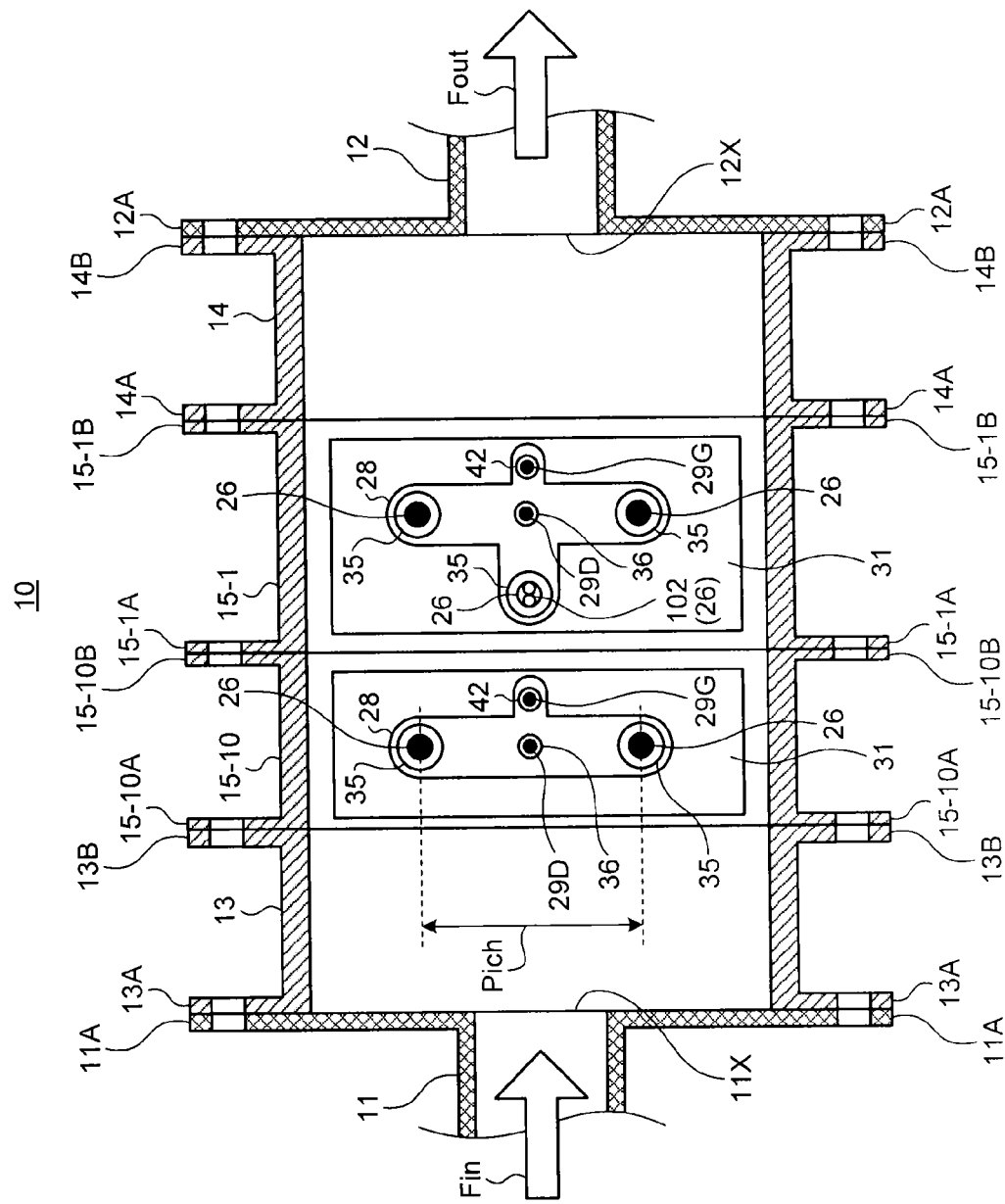
FIG. 9 is a sectional schematic diagram (an elevational view) of the ultraviolet water treatment apparatus in which the apparatus for measuring hydroxyl radicals is installed in the second embodiment.

FIG. 9 is a sectional schematic diagram (an elevational view) of the ultraviolet water treatment apparatus in which the apparatus for measuring hydroxyl radicals of the second embodiment is installed.

A configuration of an apparatus 100A for measuring hydroxyl radicals of the second embodiment will be described first.

An apparatus main body 101X for measuring hydroxyl radicals forming the apparatus 100A for measuring hydroxyl radicals broadly includes a first main body 101A and a second main body 101B connected to the first main body 101A through the protective pipe 26.

The first main body 101A includes the pump 104 for diverting and taking in the water to be treated as the liquid to be treated flowing through the water flowing barrel through the intake pipe 103, the shutoff valve 105 for shutting off the intake of the water to be treated by the pump 104 in accordance with needs such as maintenance, and the reagent adding device 106 for adding the hydroxyl radical measuring reagent to the water to be treated taken in.

The second main body 101B includes the spectroscopic analyzer 107 to which the water to be treated with the hydroxyl radical measuring reagent added thereto flows in after flowing through the protective pipe 26 and being irradiated with ultraviolet rays and that spectroscopically analyses the amount (concentration) of hydroxyl radicals produced and the discharge pipe 108 that discharges the water to be treated with the reagent added thereto after the spectroscopic analysis.

In the above configuration, the protective pipe 26 is formed of an ultraviolet transmitting material such as quartz glass.

Next, the pump 104 of the first main body 101A forming the apparatus 100A of the second embodiment for measuring hydroxyl radicals diverts and takes in the water to be treated flowing through the water flowing barrel through the intake pipe 103.

The water to be treated taken in flows in to the reagent adding device 106 through the shutoff valve 105.

The reagent adding device 106 then adds the hydroxyl radical measuring reagent to the water to be treated so as to give a certain concentration.

The water to be treated with the hydroxyl radical measuring reagent added thereto flows through the protective pipe 26, is irradiated with ultraviolet rays to produce hydroxyl radicals according to the above reaction formulae, and is guided to the spectroscopic analyzer 107 of the second main body 101B.

In this situation, the amount of flow of the water to be treated flowing through the protective pipe 26 per unit time and the concentration of the hydroxyl radical measuring reagent are set by the spectroscopic analyzer 107 in advance. The spectroscopic analyzer 107 then continuously spectroscopically analyzes the amount (concentration) of hydroxyl radicals produced. The analysis result is sent to the managing apparatus (not illustrated), fed back, and used for the control of the amount of ultraviolet irradiation, the control of the amount of flow of the water to be treated, or the like to perform control so that the disinfection (sterilization) or oxidizing treatment on the water to be treated is performed as predetermined.

Thereafter, the water to be treated with the hydroxyl radical measuring reagent added thereto for which the spectroscopic analysis has been completed is not returned to the water flowing barrel and is discharged through the discharge pipe 108 or is subjected to waste liquid treatment as needed and is discharged.

[3] Third Embodiment

The above embodiments employ a configuration in which the water to be treated with the hydroxyl radical measuring reagent added thereto flows along the extension direction of the ultraviolet lamps 25. However, the present third embodiment employs a configuration in which the water to be treated with the hydroxyl radical measuring reagent added thereto flows along a direction crossing the extension direction of the ultraviolet lamps 25.

Figure 10:
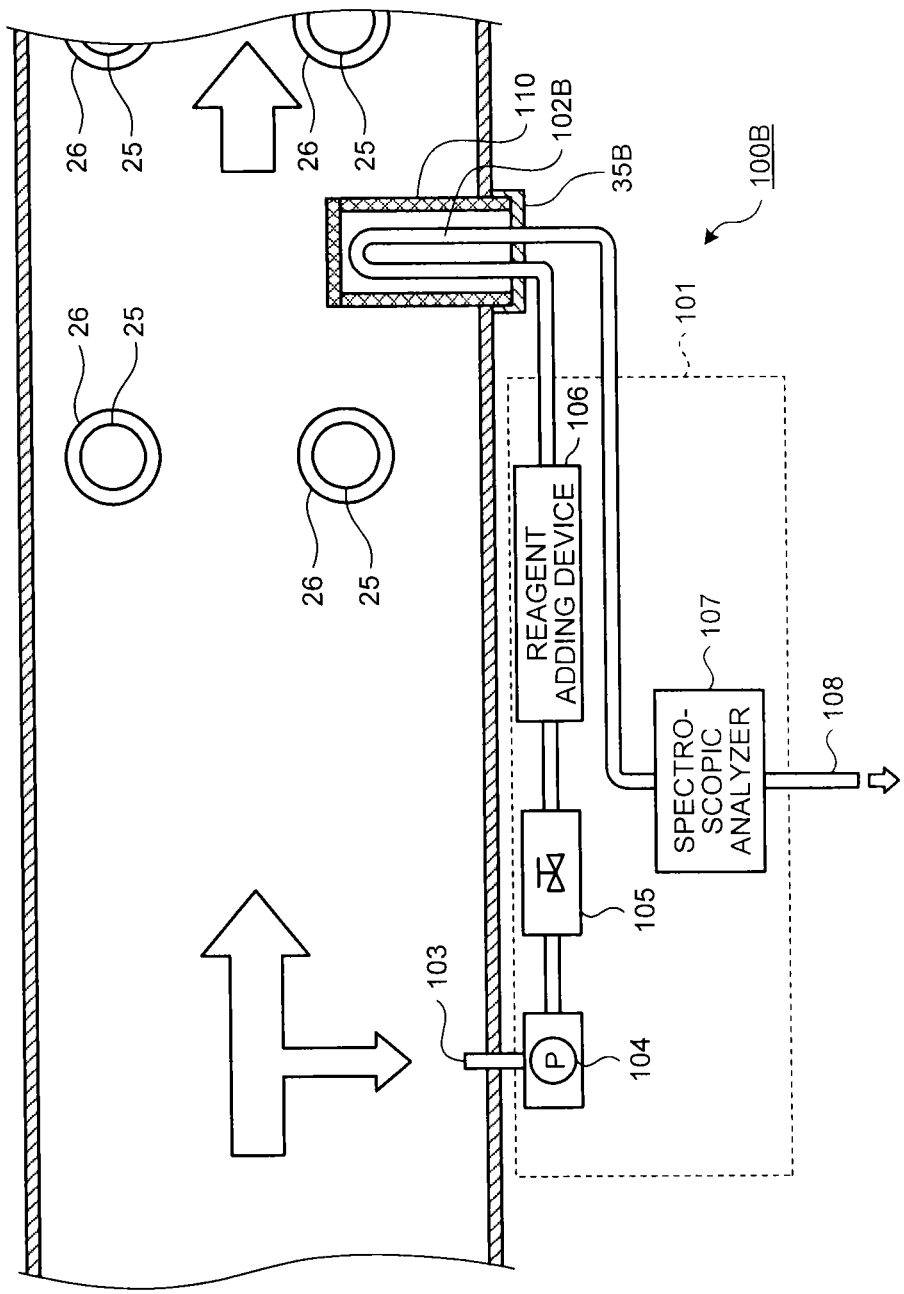
FIG. 10 is an illustrative diagram of a diagrammatic configuration of an apparatus for measuring hydroxyl radicals according to a third embodiment.

FIG. 10 is an illustrative diagram of a diagrammatic configuration of an apparatus for measuring hydroxyl radicals of the third embodiment.

As illustrated in FIG. 10, a hydroxyl radical measuring probe 110 forming this apparatus 100B for measuring hydroxyl radicals of the third embodiment is formed to protrude into the water flowing barrel along the direction crossing the extension direction of the ultraviolet lamps 25.

The hydroxyl radical measuring probe 110 is formed of an ultraviolet transmitting material such as quartz glass. A diverting pipe 102B for measurement, in place of the diverting pipe 102 for measurement of the first embodiment, is integrally incorporated into the hydroxyl radical measuring probe 110.

With this configuration, similarly to the first embodiment, the pump 104 of the apparatus 100B for measuring hydroxyl radicals diverts and takes in the water to be treated flowing through the water flowing barrel through the intake pipe 103.

The water to be treated taken in flows in to the reagent adding device 106 through the shutoff valve 105. The reagent adding device 106 then adds the hydroxyl radical measuring reagent to the water to be treated so as to give a certain concentration.

The water to be treated with the hydroxyl radical measuring reagent added thereto flows through the diverting pipe 102B for measurement. The water is then irradiated with ultraviolet rays within the hydroxyl radical measuring probe 110 to produce hydroxyl radicals according to the above reaction formulae, and is guided to the spectroscopic analyzer 107.

In this situation, the amount of flow of the water to be treated flowing through the diverting pipe 102B for measurement per unit time and the concentration of the hydroxyl radical measuring reagent are set by the spectroscopic analyzer 107 in advance. The spectroscopic analyzer 107 then continuously spectroscopically analyzes the amount (concentration) of hydroxyl radicals produced; and the analysis result is sent to the managing apparatus (not illustrated). The sent analysis result is fed back and is used for the control of the amount of ultraviolet irradiation, the control of the amount of flow of the water to be treated, or the like to perform control so that the disinfection (sterilization) or oxidizing treatment on the water to be treated is performed as predetermined.

Thereafter, the water to be treated with the hydroxyl radical measuring reagent added thereto for which the spectroscopic analysis has been completed is not returned to the water flowing barrel and is discharged through the discharge pipe 108 or is subjected to waste liquid treatment as needed and is discharged.

As described above, the present third embodiment can also measure hydroxyl radials continuously without influencing the water quality or the like of a treatment system in water treatment facilities or the like.

The diverting pipe 102B for measurement, which has a structure housed in the protective pipe 26, allows the operation of the ultraviolet water treatment apparatus to be continued even when replacement or maintenance is performed, and improves the operation efficiency of the ultraviolet water treatment apparatus.

[4] Effects of Embodiments

As described above, each of the embodiments, in the ultraviolet treatment apparatus that performs accelerated oxidation water treatment using ultraviolet irradiation, diverts and takes in the water to be treated with the pro-oxidant that produces hydroxyl radicals by ultraviolet irradiation such as ozone, hydrogen peroxide, and chlorine agents such as sodium hypochlorite added thereto in advance before ultraviolet irradiation; adds the hydroxyl radical measuring reagent to the water to be treated; and irradiates the water to be treated with ultraviolet rays from an ultraviolet irradiation source within the water flowing barrel (reaction tank) in a state partitioned by the protective pipe, thereby achieving hydroxyl radical measurement using the reagent continuously and automatically for the produced hydroxyl radicals immediately and with the treatment continued.

Consequently, hydroxyl radical concentration is continuously measured with the water treatment continued, and by its result, the amount of addition of the pro-oxidant, the amount of ultraviolet irradiation, and the like are adjusted, thereby achieving necessary and sufficient treatment and preventing unnecessary addition of pro-oxidant and power consumption.

Modification of Embodiments

Although each of the above embodiments diverts the water to be treated flowing through the apparatus for measuring hydroxyl radicals in the ultraviolet irradiation apparatus, it can also be configured that, for example, the water to be treated is diverted from the upstream side of the inlet pipe 13 such as the inflow side connection pipe 11.

Although the foregoing describes the embodiments of the present invention, these embodiments are presented as examples and do not intend to limit the scope of the invention. These novel embodiments can be performed in various other forms, and various omissions, replacements, and changes can be made without departing from the essence of the invention. These embodiments and modifications thereof are included in the scope and essence of the invention and are included in the inventions described in the claims and equivalents thereof.

EXAMPLES

The following describes an example using a terephthalic acid solution as the hydroxyl radical measuring reagent.

The terephthalic acid solution was obtained by dissolving powdery terephthalic acid in an aqueous sodium hydroxide solution with a pH of about 11, and an aqueous solution of 1 mmol/L was obtained. This solution, as the hydroxyl radical measuring reagent, was added to the water to be treated so as to give a concentration after addition of 0.01 mmol/L.

The terephthalic acid solution was added as the hydroxyl radical measuring reagent to the water to be treated (pure water in the present example) with hydrogen peroxide as the pro-oxidant added in advance to produce hydroxyl radicals by ultraviolet irradiation so as to give a concentration of 0.05%.

In the present example, the solution with hydrogen peroxide and the terephthalic acid solution added thereto was irradiated with ultraviolet rays with an ultraviolet intensity of 2 mW/cm$^2$ for 1 minute and was treated so as to give an amount of ultraviolet irradiation of 120 mJ/cm$^2$.

The fluorescence intensity of the treated water after irradiation was measured to give a fluorescence intensity of 500 (an output value of an analyzer) with an excitation wavelength of 310 nm and a fluorescence wavelength of 425 nm.

The value was 4,000 times or larger than that in a case of ultraviolet rays alone and about 5,000 times with respect to that in a case of hydrogen peroxide alone, which reveals that hydroxyl radicals can be measured selectively and continuously.

The invention claimed is:

1. An apparatus for measuring hydroxyl radicals produced by irradiating a liquid flowing in a main channel with ultraviolet rays from an ultraviolet lamp placed in the main channel, the apparatus comprising:
   a diverging unit including a divergent channel, that is made of a UV transmitting material, diverging from the main channel such that a part of the liquid flowing in the main channel is diverted for hydroxyl radicals measurement, the divergent channel including a portion extending into the main channel to oppose the ultraviolet lamp positioned in the main channel such that the part of the liquid is irradiated with an ultraviolet ray from the ultraviolet lamp and the divergent channel extending back out of the main channel such that the irradiated liquid is guided outside of the main channel;
   a reagent adder placed in the divergent channel upstream of the portion, the reagent adder configured to add a hydroxyl radical measuring reagent to the part of the liquid before the ultraviolet ray irradiation; and
   an analyzer placed in the divergent channel downstream of where the divergent channel exits the main channel, the analyzer configured to measure an amount of hydroxyl radicals produced from the part of the liquid by the ultraviolet ray irradiation, based on a change in the hydroxyl radical measuring reagent before and after the ultraviolet ray irradiation.

2. The apparatus of claim 1, wherein the analyzer includes a spectroscopic analyzer configured to continuously perform spectroscopic analysis of the part of the liquid.

3. The apparatus of claim 2, wherein the hydroxyl radical measuring reagent is a terephthalic acid solution.

4. The apparatus of claim 1, wherein the portion of the divergent channel extends in an extending direction of the ultraviolet lamp in the main channel.

5. The apparatus of claim 1, wherein the portion of the divergent channel extends in a direction crossing an extending direction of the ultraviolet lamp in the main channel.

6. A liquid treatment apparatus, comprising:
   a water flowing barrel connected to an external pipe and forming a main channel through which a liquid introduced from the external pipe flows;
   an ultraviolet irradiation unit provided in the water flowing barrel and including an ultraviolet lamp configured to irradiate the liquid with ultraviolet rays;
   a diverting unit including a divergent channel, that is made of a UV transmitting material, diverging from the main channel such that a part of the liquid flowing in the water flowing barrel is diverted from the main channel for hydroxyl radicals measurement, the divergent channel including a portion extending into the water flowing barrel and extending back out of the water flowing barrel such that the part of the liquid is irradiated with an ultraviolet ray from the ultraviolet lamp and the irradiated liquid is guided outside of the water flowing barrel;
   a reagent adder placed in the divergent channel upstream of the portion, the reagent adder configured to add a hydroxyl radical measuring reagent to the part of the liquid before the ultraviolet ray irradiation; and
   an analyzer placed in the divergent channel downstream of where the divergent channel exits the water flowing barrel, the analyzer configured to measure an amount of hydroxyl radicals produced from the part of the liquid by the ultraviolet ray irradiation, based on a change in the hydroxyl radical measuring reagent before and after the ultraviolet ray irradiation.

* * * * *